US009090556B2

(12) United States Patent
Miller et al.

(10) Patent No.: US 9,090,556 B2
(45) Date of Patent: Jul. 28, 2015

(54) METHOD FOR PRODUCING ACYLOXY CARBOXYLIC ACIDS AND DERIVATIVES THEREOF

(71) Applicant: BOARD OF TRUSTEES OF MICHIGAN STATE UNIVERSITY, East Lansing, MI (US)

(72) Inventors: Dennis Miller, Okemos, MI (US); Carl T. Lira, East Lansing, MI (US); Lars Peereboom, Haslett, MI (US); Aspi K. Kolah, Mason, MI (US)

(73) Assignee: BOARD OF TRUSTEES OF MICHIGAN STATE UNIVERSITY, East Lansing, MI (US)

(*) Notice: Subject to any disclaimer, the term of this patent is extended or adjusted under 35 U.S.C. 154(b) by 36 days.

(21) Appl. No.: 13/707,735

(22) Filed: Dec. 7, 2012

(65) Prior Publication Data
US 2013/0150619 A1 Jun. 13, 2013

Related U.S. Application Data

(60) Provisional application No. 61/568,726, filed on Dec. 9, 2011.

(51) Int. Cl.
C07C 67/08 (2006.01)
(52) U.S. Cl.
CPC .................................. *C07C 67/08* (2013.01)
(58) Field of Classification Search
None
See application file for complete search history.

(56) References Cited

U.S. PATENT DOCUMENTS

| 2,399,595 | A | * | 4/1946 | Filachione et al. | 560/266 |
| 6,693,213 | B1 | * | 2/2004 | Kolena et al. | 560/265 |
| 6,713,640 | B2 | | 3/2004 | Miller et al. | |
| 6,992,209 | B2 | | 1/2006 | Lilga et al. | |
| 7,321,052 | B2 | | 1/2008 | Miller et al. | |
| 7,329,774 | B2 | * | 2/2008 | Zuber et al. | 560/231 |

OTHER PUBLICATIONS

Abstract of GB 603189.*
Smith et al., "Pyrolysis of Lactic Acid Derivatives," Industrial and Engineering Chemistry, vol. 34, No. 4, p. 473-479 (1942).
Fisher et al., "Methyl Acrylate Production by Pyrolysis of Methyl Acetoxypropionate," Industrial and Engineering Chemistry, vol. 36, No. 3, p. 229-234 (1944).
Ratchford et al., "Methyl Acrylate by Pyrolysis of Methyl Acetoxypropionate," Industrial and Engineering Chemistry, vol. 37, No. 4, p. 382-387 (1945).
Filachione et al., "Preparation of a-Carbalkoxyalkyl Methacrylates by Pyrolysis of of the Corresponding a-Acetoxyisobutyrates," Industrial and Engineering Chemistry, vol. 70, p. 526-529 (1948).
Golomb et al., "The Acyl Derivatives and Lactides of Some a-Hydroxy-acids," Journal of the Chemical Society, p. 838-847 (1962).

* cited by examiner

*Primary Examiner* — Karl J Puttlitz
(74) *Attorney, Agent, or Firm* — Marshall, Gerstein & Borun LLP

(57) ABSTRACT

The disclosure relates to a process for forming an acyloxy carboxylic acid or a derivative of the acid. A hydroxy acid compound is reacted with a carboxylic acid in a reaction vessel and in the presence of a catalyst, such as in a reactive distillation column containing the catalyst. The reaction product formed in the reaction vessel includes an acyloxy carboxylic acid compound, which can be removed continuously from the vessel in a product stream. Another product stream containing unreacted (excess) carboxylic acid and/or reaction byproducts such as water can be separately removed continuously from the reaction vessel.

24 Claims, 3 Drawing Sheets

METHOD FOR PRODUCING ACYLOXY CARBOXYLIC ACIDS AND DERIVATIVES THEREOF

CROSS REFERENCE TO RELATED APPLICATION

Priority is claimed to U.S. Provisional Application No. 61/568,726 (filed on Dec. 9, 2011), which is incorporated herein by reference in its entirety.

STATEMENT OF GOVERNMENT INTEREST

None.

BACKGROUND OF THE DISCLOSURE

1. Field of the Disclosure

The disclosure generally relates to the formation of an acyloxy carboxylic acid compound by reaction of a hydroxy acid compound with a carboxylic acid (e.g., 2-acetoxy propanoic acid formed from lactic acid and acetic acid). The reaction can be performed in a reactive distillation column to provide improved reactant conversion and product yield.

2. Brief Description of Related Technology

Filachione et al. U.S. Pat. No. 2,399,595 discloses a process for manufacturing acyloxy carboxylic acids. Batch reaction of a hydroxy carboxylic acid with a carboxylic acid in the presence of a catalyst and an entraining agent forms the acyloxy carboxylic acid product. The exemplified batch processes result in product yields ranging from about 50% to about 80%.

Lilga et al. U.S. Pat. No. 6,992,209 discloses methods for forming α-,β-unsaturated acids and esters from a corresponding α-acyloxy carboxylic acid. Reaction of an α-hydroxy carboxylic acid or ester with a carboxylic acid in the presence of a catalyst forms the α-acyloxy carboxylic acid. The exemplified batch processes result in combined product and product derivative yields ranging from about 90% to about 95% using a large excess of the carboxylic acid.

SUMMARY

The disclosure relates to a process for forming an acyloxy carboxylic acid or a derivative of the acid. A hydroxy acid compound is reacted with a carboxylic acid in a reaction vessel or mixture and in the presence of a catalyst, such as in a reactive distillation column containing the catalyst. The reaction product formed in the reaction vessel includes an acyloxy carboxylic acid compound, which can be removed continuously from the vessel in a product stream. Another product stream containing unreacted (excess) carboxylic acid and/or reaction byproducts such as water can be separately removed continuously from the reaction vessel. The disclosed process provides several advantages over prior approaches to forming acyloxy carboxylic acids, including: lower carboxylic acid feed, high hydroxy acid conversion, high acyloxy carboxylic acid product yield, low water content of the acyloxy carboxylic acid product stream, and high-temperature/high-rate operation.

In one aspect, the disclosure relates to a method for forming an acyloxy carboxylic acid or derivative thereof, the method comprising: (a) providing a first reactant stream comprising a hydroxy acid selected from the group consisting of an α-hydroxy carboxylic acid compound, a β-hydroxy carboxylic acid compound, and combinations thereof; (b) providing a second reactant stream comprising a carboxylic acid; (c) feeding the first reactant stream and the second reactant stream to a reaction vessel containing a catalyst; (d) reacting the hydroxy acid and the carboxylic acid in the reaction vessel and in the presence of the catalyst to form a reaction product therebetween, the reaction product comprising an acyloxy carboxylic acid compound; and (e) removing a first product stream comprising the acyloxy carboxylic acid compound from the reaction vessel; and (f) optionally removing a second product stream comprising unreacted carboxylic acid from the reaction vessel. In a refinement, a ratio of the carboxylic acid to the hydroxy acid fed to the reaction vessel ranges from 1:1 to 10:1. In another refinement, the first product stream is substantially free from water. In another refinement, the reaction of the hydroxy acid and the carboxylic acid in the presence of the catalyst is performed substantially at or above the bubble point of a local mixture in the reaction vessel between the first reactant stream, the second reactant stream, and any reaction products therebetween. In another refinement, the hydroxy acid has a conversion of at least 95%. In another refinement, (i) the first product stream further comprises unreacted carboxylic acid; and (ii) the method further comprises: (g) separating the acyloxy carboxylic acid compound from the unreacted carboxylic acid. In another refinement, (i) the method comprises removing the second product stream in part (f); and (ii) the method further comprises: (g) recycling the second product stream to the reaction vessel to provide at least a portion of the carboxylic acid in the second reactant stream.

In another aspect, (i) the hydroxy acid comprises the α-hydroxy carboxylic acid compound (e.g., lactic acid); and (ii) the reaction product comprises a 2-acyloxy carboxylic acid compound (e.g., 2-acetoxy propanoic acid when the carboxylic acid comprises acetic acid). In a refinement, (i) the α-hydroxy carboxylic acid compound comprises a first compound having the formula (I):

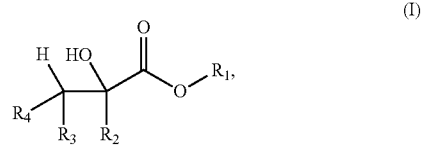

wherein: (A) $R_1$ is selected from the group consisting of H, hydrocarbons containing from 1 to 20 carbon atoms, and heteroatom-substituted hydrocarbons containing from 1 to 20 carbon atoms, and (B) each of $R_2$, $R_3$, and $R_4$ are independently selected from the group consisting of H, hydrocarbons containing from 1 to 20 carbon atoms, and heteroatom-substituted hydrocarbons containing from 1 to 20 carbon atoms; (ii) the carboxylic acid comprises a second compound having the formula (II):

wherein $R_5$ is independently selected from the group consisting of H, hydrocarbons containing from 1 to 20 carbon atoms, and heteroatom-substituted hydrocarbons containing from 1 to 20 carbon atoms; and (iii) the 2-acyloxy carboxylic acid compound comprises a third compound having the formula (III):

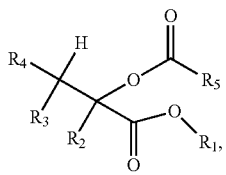

(III)

wherein $R_1$ to $R_5$ are as defined in formula (I) and formula (II). In yet another aspect, (i) the hydroxy acid comprises the β-hydroxy carboxylic acid compound (e.g., 3-hydroxy propanoic acid); and (ii) the reaction product comprises a 3-acyloxy carboxylic acid compound (e.g., 3-acetoxy propanoic acid when the carboxylic acid comprises acetic acid).

Various refinements and extensions of the foregoing methods and compositions are possible. For example, the catalyst can comprise an acid catalyst (e.g., a solid acid catalyst). The acyloxy carboxylic acid compound can have a yield of at least 80%, 90%, or 95%. The first product stream can have a water concentration of 0.1 wt. % or less. In an embodiment, the reaction vessel comprises a continuous reactive distillation column and the catalyst comprises a solid acid catalyst, for example where water is present in a local region of the reactive distillation column where substantial hydroxy acid is present, the water being present in an amount sufficient to reduce oligomerization of the hydroxy acid in the local region. In a particular embodiment, (i) the reaction vessel comprises (A) a first inlet positioned at a first elevation, (B) a second inlet positioned at a second elevation lower than the first elevation, (C) a first outlet positioned at a third elevation lower than the second elevation; and (D) optionally a second outlet position at a fourth elevation higher than the first elevation; (ii) at least some of the solid acid catalyst is positioned in the reaction vessel between the first inlet and the second inlet; (iii) the first reactant stream is fed to the reaction vessel through the first inlet; (iv) the second reactant stream is fed to the reaction vessel through the second inlet; (v) the first product stream is removed from the reaction vessel through the first outlet; and (vi) the second product stream, when present, is removed from the reaction vessel through the second outlet. In an embodiment, the first reactant stream comprises the hydroxy acid in an amount ranging from 5 wt. % to 100 wt. %; in a further refinement, the first reactant stream comprises (i) the hydroxy acid in an amount ranging from 5 wt. % to 50 wt. % and (ii) water in an amount ranging from 50 wt. % to 95 wt. %. In an embodiment, the first reactant stream comprises oligomers of the hydroxy acid in an amount of 10 wt. % or less relative to monomers of the hydroxy acid in the first reactant stream. In one refinement, the first reactant stream comprises an equilibrium mixture of the hydroxy acid and its associated oligomers. In an alternative refinement, the first reactant stream comprises a non-equilibrium mixture of the hydroxy acid and its associated oligomers, such as where the oligomer content of the first reactant stream is 50% or less relative to the oligomer content of a corresponding equilibrium mixture of the hydroxy acid and its associated oligomers. In another embodiment, the first product stream comprises oligomers of the acyloxy carboxylic acid compound in an amount of 10 wt. % or less relative to monomers of the acyloxy carboxylic acid compound in the first product stream.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

Figure 1:
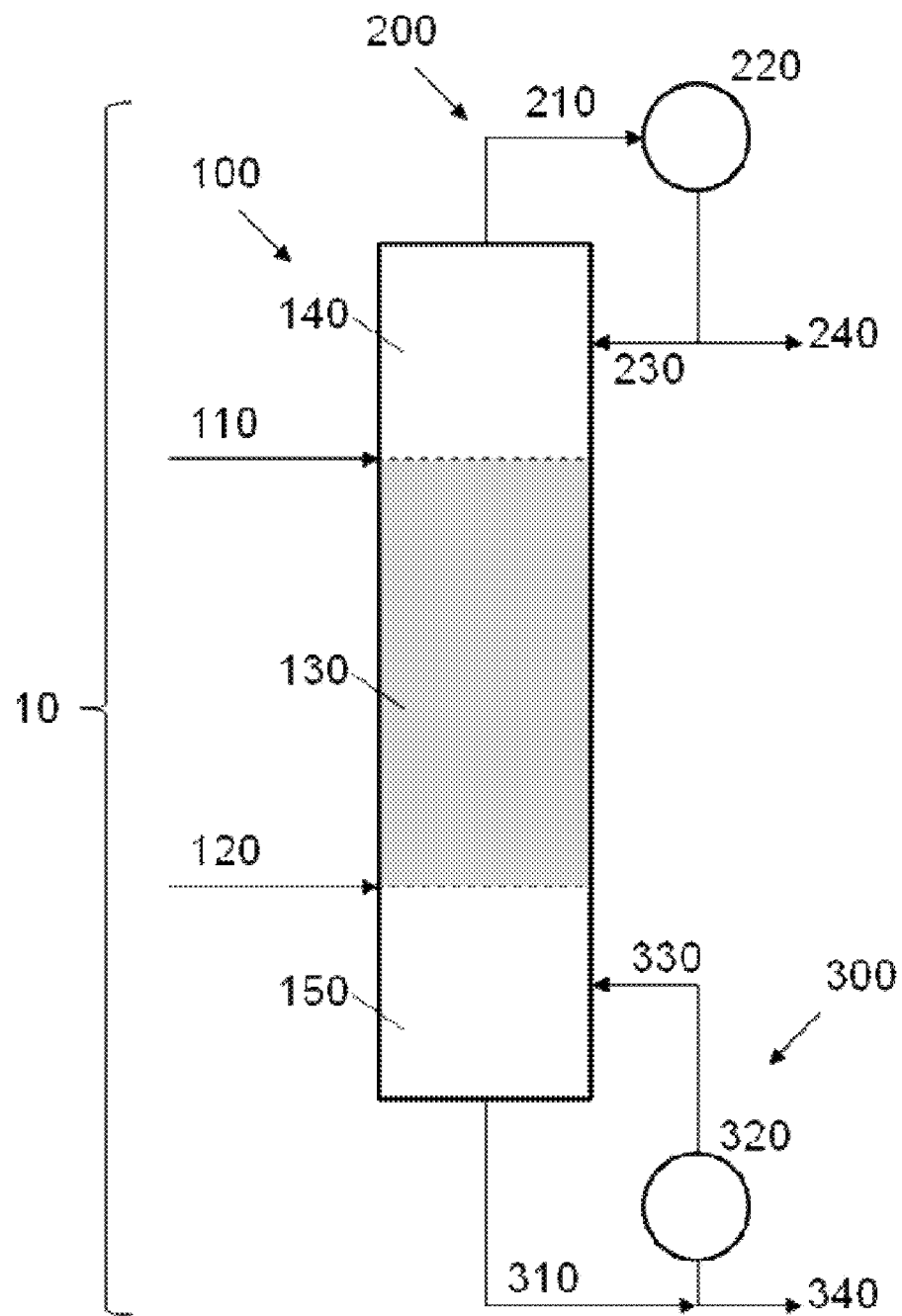
FIG. 1 illustrates a reactive distillation reactor system for forming acyloxy carboxylic acid compounds according to the disclosure.

While the disclosed processes, compositions, and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The disclosure relates to a process for forming an acyloxy carboxylic acid or a derivative of the acid (e.g., an acyloxy carboxylic acid ester). A hydroxy acid compound (e.g., α-hydroxy carboxylic acid compound, a β-hydroxy carboxylic acid compound, or combinations/mixtures thereof) is reacted with a carboxylic acid in a reaction vessel and in the presence of a catalyst, such as where the reactants are fed continuously in the same or different streams to a reaction vessel containing the catalyst. The reaction product formed in the reaction vessel includes an acyloxy carboxylic acid compound, which is suitably removed continuously from the vessel in a product stream. Another product stream containing unreacted (excess) carboxylic acid and/or reaction byproducts such as water can be separately removed continuously from the reaction vessel.

The disclosed process provides several advantages over prior approaches to forming acyloxy carboxylic acids. A relatively low molar excess of the carboxylic acid can be used while still obtaining high levels of hydroxy acid conversion and acyloxy carboxylic acid compound product yield. This reduces the net amount of the carboxylic acid fed to the reaction vessel, which in turn can reduce the effort and cost of downstream separation and recycling of unreacted carboxylic acid (e.g., separation from water or acyloxy carboxylic acid product for re-use as a reactant) and can increase the efficiency of the reaction vessel (e.g., in terms of rate of product formation per unit reactor volume). The process also can yield acyloxy carboxylic acid product streams that are relatively free from water (e.g., whether as fed to the reactor or formed as a condensation reaction byproduct), thus protecting the acyloxy carboxylic acid product from undesired hydrolysis and decomposition. The process can be operated at relatively high temperatures (e.g., at or near the bubble point of the reaction mixture) while avoiding product hydrolysis, thus enhancing the reaction rate and rate of product formation per unit of reaction volume. The process provides a method for minimizing the oligomeric content of its hydroxy acid feed across a wide range of feed concentrations, thereby increasing the yield of the desired monomeric form of the acyloxy carboxylic acid compound and reducing the formation of its oligomeric counterparts.

FIG. 1 illustrates an embodiment of the disclosed process using a continuous reactive distillation system 10 with a reactive distillation column 100 as the reaction vessel. The vessel 100 includes a first inlet 110 and a second inlet 120 for feeding reactant streams to the vessel 100. Suitably, a first reactant stream including the hydroxy acid is fed via the first inlet 110 and a second reactant stream including the carboxylic acid is fed via the second inlet 120, such as when the carboxylic acid is relatively more volatile than the hydroxy acid (e.g., where the carboxylic acid moves upwardly through the reactive distillation column 100 and counter-currently to the hydroxy acid moving downwardly. Alternatively, a first reactant stream including the carboxylic acid is fed via the first inlet 110 and a second reactant stream including the hydroxy acid is fed via the second inlet 120, such as when the carboxylic acid is relatively less volatile than the hydroxy acid (e.g., where the carboxylic acid moves downwardly through the reactive distillation column 100 and counter-currently to the hydroxy acid moving upwardly). The reactants can be fed to the vessel in liquid form (e.g., at ambient temperature or preheated to within 10° C. or 20° C. of their boiling points) or vapor form. In other embodiments (not shown), the vessel 100 may include a single inlet through which both reactants are co-fed (e.g., where the carboxylic acid and hydroxy acid are co-fed through the inlet 110 and travel downwardly while water is continuously removed and stripped via the overhead portion 200). As illustrated, the vessel 100 can include three interior zones: a reaction zone 130 where the bulk of the acyloxy carboxylic acid compound product is formed, an upper (rectifying) zone 140, and a lower (stripping) zone 150. The reaction zone 130 also includes the reaction catalyst, for example in the form of a solid catalyst packing supported in the reaction zone 130. In the shown spatial arrangement, the first inlet 110 is positioned at a first elevation, the second inlet 120 is positioned at a second elevation lower than the first elevation, and at least some of the reaction zone 130 is positioned between the inlets 110, 120 (e.g., where high and low elevations are relative spatial terms defined in relation to gravity vector for given reaction orientation/installation during use). More generally, the inlets 110, 120 can be positioned at any convenient location(s) on the vessel 100 relative to the zones 130, 140, 150.

The reactive distillation system 10 further includes an overhead/reflux portion 200 and a bottoms/reboiler portion 300 for product recycle and recovery. An overhead vapor stream 210 (e.g., including water and/or unreacted carboxylic acid) is removed from the upper zone 140 of the vessel 100 (e.g., at or above the first inlet 110) and then condensed in a reflux condenser 220 to form a liquid stream, a portion of which is returned to the vessel 100 as a reflux stream 230 and another portion of which is withdrawn as a second product stream 240. A bottoms liquid stream 310 (e.g., including the acyloxy carboxylic acid compound and potentially unreacted carboxylic acid or hydroxy acid) is removed from the lower zone 150 of the vessel 100 (e.g., at or below the second inlet 120), a portion of which is vaporized in a reboiler 320 and returned to the vessel 100 as a reboiler stream 330 and another portion of which is withdrawn as a first product stream 340.

Other general features of continuous reactive distillation are disclosed in Miller et al. U.S. Pat. Nos. 6,713,640 and 7,321,052, incorporated by reference herein in their entireties.

The catalyst is suitably an acid catalyst, for example a mineral acid or a solid acid catalyst capable of donating a proton as a Brønsted acid. A liquid acid catalyst can be continuously fed to the reaction vessel 100 (e.g., as a component of one or both of the reactant streams). A solid acid catalyst can be mounted within the reaction vessel 100 (e.g., as a supported packing in the reaction zone 130) to allow a continuous reaction without a continuous feed of a liquid acid catalyst. Suitable strong acid catalysts can include sulfuric acid, toluene-sulfonic acid, polysulfonic acid, phosphoric acid, and polyphosphoric acid. Suitable solid acid catalysts can include ion exchange resins in acid form (e.g., an AMBERLYST resin available from Rohm and Haas, Philadelphia, Pa.) or zeolite catalysts.

The operating temperature within the reaction vessel 100 is desirably selected to be at, near, or above the bubble point of the reaction mixture. High reaction temperatures and continuous water removal (e.g., water formed as a condensation product and/or co-fed with a reactant) improve reaction kinetics while avoiding hydrolysis and degradation of the acyloxy carboxylic acid compound product. For example, the operating temperature can be selected to be within +/−5° C., 10° C., or 15° C. of the bubble point of a local mixture in the reaction vessel (e.g., between reactants and products present in a localized region of the reaction vessel). Suitably, the reaction vessel 100 is operated in distillation mode, such that the local temperature within the column is determined by the bubble point of the local composition in the column and the selected column operating pressure. The reboiler 320 temperature can be selected to obtain the desired temperature distribution within the reaction zone 130 as well as to control the water and carboxylic acid content of the various bottoms stream 310, 330, and 340 (e.g., where low or negligible water limits product hydrolysis and the presence of excess, unreacted carboxylic acid limits excessive temperatures leading to product breakdown). In the particular lactic acid/acetic acid reaction system illustrated in the examples below, suitable temperatures in the reaction zone 130 of the vessel 100 can be at least 105° C., 110° C., 115° C., 120° C., 125° C., or 130° C. and/or up to 120° C., 125° C., 130° C., or 140° C. (e.g., varying as a function of position in the reaction zone 130). Similarly, suitable reboiler temperatures can be at least 120° C., 125° C., 130° C., or 140° C. and/or up to 160° C., 180° C., 190° C., or 200° C. for the lactic acid/acetic acid reaction system.

Reactants

The hydroxy acid reactant is not particularly limited and can generally include organic compounds having a carboxylic acid (—COOH) functional group or derivative thereof (e.g., a single moiety as a terminal group on the molecule) and a hydroxyl (—OH) functional group (e.g., a single hydroxyl moiety on the molecule). The hydroxy acid can generally have from 2 to 20 carbon atoms (e.g., at least 2, 3, or 4 and/or up to 5, 10, 15, or 20), for example being a saturated or unsaturated, linear or branched alkyl hydrocarbon with or without heteroatoms (e.g., N, O, S) as a base molecule structure for the carboxylic acid and hydroxyl functional groups. The hydroxyl group is suitably positioned on the hydroxy acid molecule such that the hydroxy acid generally is not susceptible to the formation of internal cyclic esters with its own acid group. For example, the hydroxyl group can be positioned on a carbon atom adjacent the carbonyl carbon of the acid group (i.e., an α-hydroxy carboxylic acid compound), or the hydroxyl group can be positioned on a carbon atom with one additional intervening carbon atom adjacent the carbonyl carbon of the acid group (i.e., a β-hydroxy carboxylic acid compound). In an embodiment, the hydroxy acid is suitably in acid form. In other embodiments, the hydroxy acid is in an acid derivative form. The functional group forming the acid derivative is not particularly limited (e.g., including amides or esters, such as with an additional 1 to 5 carbon atoms) and can limit the potential for hydroxy acid oligomerization, but the acid derivative is suitably selected to avoid catalyst deactivation during reaction. Accordingly, hydroxy acids (e.g., α-hydroxy carboxylic acid compounds and/or β-hydroxy carboxylic acid compounds) according to the disclosure generally include the hydroxy acid in its acid form or its acid derivative form.

A representative structure of an α-hydroxy carboxylic acid compound according to the disclosure is shown in Formula I.A below:

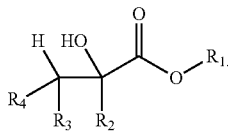

(I.A)

A representative structure of a β-hydroxy carboxylic acid compound according to the disclosure is shown in Formula I.B below:

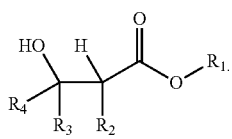

(I.B)

In Formulas I.A and I.B, $R_1$ can be —H (i.e., acid form), a hydrocarbon containing from 1 to 20 carbon atoms (e.g., at least 1, 2, or 3 and/or up to 4, 5, 6, 8, 10, 15, or 20), and heteroatom-substituted hydrocarbons containing from 1 to 20 carbon atoms (e.g., at least 1, 2, or 3 and/or up to 4, 5, 6, 8, 10, 15, or 20). In an embodiment, $R_1$ can be —$CH_3$ or —$C_2H_5$ (i.e., a methyl or ethyl ester derivative). $R_2$, $R_3$, and $R_4$ can be independently selected from the same general groups as $R_1$. In an embodiment, $R_1$-$R_4$ are —H, in which case the α-hydroxy carboxylic acid compound represents 2-hydroxy propanoic acid (e.g., lactic acid in either or both isomeric forms) and the β-hydroxy carboxylic acid compound represents 3-hydroxy propanoic acid.

The hydroxy acid can be fed to the reaction vessel at any desired concentration in the first reactant stream. For example, the concentration of the hydroxy acid in the first reactant stream can range from 1 wt. % to 100 wt. % (e.g., at least 1%, 5%, 10%, 15%, 20%, 30%, 40%, 50%, 60%, 70%, 80% or 90% and/or up to 15%, 20%, 25%, 30%, 50%, 60%, 80%, 90%, 95%, or 100%). The first reactant stream can be an aqueous solution of the hydroxy acid, such as where the balance or substantial balance of the first reactant stream is water. In an embodiment, first reactant stream has a hydroxy acid concentration ranging from 5 wt. % to 50 wt. % (e.g., 10 wt. % to 30 wt. %) and has a water concentration ranging from 50 wt. % to 95 wt. % (e.g., 70 wt. % to 90 wt. %). The hydroxy acid concentrations can be based on the amount of hydroxy acid relative to the first reactant stream as a whole or relative to the combined amount of the hydroxy acid and water in the first reactant stream (e.g., to account for potential other constituents in the feed stream).

Hydroxy acids in their acid form are prone to the formation of oligomers (e.g., ester formation between the acid group of a first molecule and the hydroxyl group of a second molecule). The degree of oligomer formation generally increases at higher hydroxy acid concentrations and at longer storage times, where hydroxy acids can achieve an equilibrium distribution between monomeric forms of the hydroxy acid and oligomeric species of varying lengths (e.g., having at least 2 repeating units, such as from 2-5 or 2-10 repeating units). Oligomer formation of the hydroxy acid reactant is generally undesirable, as the basic oligomeric structure can propagate through the reaction system to yield an acyloxy carboxylic acid compound product that includes monomeric forms (often a desirable form) and oligomeric forms (often an undesirable form).

To this end, the first reactant stream (or more generally all reactant streams fed to the reaction vessel) suitably has a hydroxy acid oligomer content of 10%, 5%, 2%, or 1% or less and/or at least 0.1%, 0.2%, 0.5%, or 1% (e.g., representing an equilibrium or non-equilibrium distribution of monomeric and oligomeric species). The hydroxy acid oligomer content can be expressed on a weight basis or a molar basis, either relative to just the monomer content of the reactant stream(s) or all combined monomeric and oligomeric forms in the reactant stream(s).

For a given hydroxy acid, the equilibrium distribution of a relatively dilute solution favors the monomeric form of the hydroxy acid. Thus, in one embodiment, a low-oligomer hydroxy acid feed is provided in the form of a dilute hydroxy acid feed at equilibrium between its monomeric and oligomeric species. For example, a 10 wt. % to 30 wt. % lactic acid in water as the hydroxy acid feed stream has a relatively low oligomer content (e.g., about 99% monomer and about 1% dimer/trimer for an equilibrium mixture of 20 wt. % lactic acid in water).

In another embodiment, a low-oligomer hydroxy acid feed is provided in the form of a concentrated hydroxy acid feed at substantial non-equilibrium between its monomeric and oligomeric species (i.e., where the departure from equilibrium is based on a higher-than-equilibrium content of the hydroxy acid monomer). As illustrated in the examples below, a general process to achieve the desired non-equilibrium mixture includes first equilibrating a low concentration mixture of the hydroxy acid in a solvent (e.g., in water) to substantially reduce oligomeric species, where the particular low concentration value is selected based on the equilibrium characteristics of the particular hydroxy acid and the desired oligomer content. The equilibration step is suitably performed at a high temperature (e.g., 80° C. to 100° C.) to increase the rate of equilibration and monomer formation. The solvent is then removed from the mixture at a low temperature (e.g., at least 10° C., 20° C., or 30° C. and/or up to 40° C., 50° C., or 60° C.) to concentrate the hydroxy acid while suppressing the rate of oligomer formation (i.e., which is kinetically limited), thus resulting in a high concentration mixture of the hydroxy acid with a substantially lower-than-equilibrium content of oligomeric species. Concentration of the hydroxy acid is suitably performed at a reduced pressure (e.g., 100 Torr, 50 Torr, or 20 Torr or less and/or at least 0.1 Torr, 1 Torr, or 10 Torr) to provide a high rate of solvent removal even at the low temperatures desirable for inhibiting oligomer formation. The concentrated non-equilibrium, low-oligomer hydroxy acid mixture can then be fed to the reaction vessel in the first reactant stream (e.g., immediately after or relatively soon after formation to limit subsequent equilibration of the mixture which would result in increased oligomer formation prior to product formation in the reaction vessel). The low oligomer content of the non-equilibrium mixture can be expressed as either an absolute amount in the first reactant stream as described above or as a relative amount compared to a corresponding equilibrium mixture of the hydroxy acid and its associated oligomers. For example, the first reactant stream suitably has an oligomer content of 50%, 40%, 30%, 20%, 10%, or 5% or less and/or at least 1%, 5%, 10%, or 20% relative to the total equilibrium oligomer content for the particular hydroxy acid under the same conditions (e.g., composition, concentration, temperature, etc.) as the first reactant stream as fed to the reaction vessel.

The carboxylic acid reactant is not particularly limited and can generally include organic compounds having a carboxylic acid (—COOH) functional group (e.g., a single moiety as a terminal group on the molecule). The carboxylic acid can generally have from 1 to 20 carbon atoms (e.g., at least 1, 2, or 3 and/or up to 5, 10, 15, or 20), for example being a saturated or unsaturated, linear or branched alkyl hydrocarbon with or without heteroatoms (e.g., N, O, S) as a base molecule structure for the carboxylic acid functional group. The carboxylic acid suitably does not contain other functional groups reactive with the carboxylic acid (—COOH) functional group (e.g., hydroxyl (—OH) or otherwise).

A representative structure of a carboxylic acid according to the disclosure is shown in Formula II below:

(II)

In Formula II, $R_5$ can be —H (i.e., formic acid), a hydrocarbon containing from 1 to 20 carbon atoms (e.g., at least 1, 2, or 3 and/or up to 4, 5, 6, 8, 10, 15, or 20), and heteroatom-substituted hydrocarbons containing from 1 to 20 carbon atoms (e.g., at least 1, 2, or 3 and/or up to 4, 5, 6, 8, 10, 15, or 20). In an embodiment, $R_5$ can be —$CH_3$ (i.e., acetic acid). In another embodiment, the carboxylic acid is selected such that it has a boiling point lower than that of the hydroxy acid to be esterified, such as where the carboxylic acid is more volatile than the hydroxy acid (e.g., where $R_5$ has from 1 to 6 carbon atoms) and travels counter-currently to the hydroxy acid through the reactive distillation column. In another embodiment, the carboxylic acid can be relatively less volatile, such that it is co-fed and travels co-currently with the hydroxy acid through the column.

The carboxylic acid can be fed to the reaction vessel at any desired concentration in the second reactant stream. Suitably, the carboxylic acid can be in essentially neat form, for example having a concentration of at least 90 wt. %, 95 wt. %, 98 wt. %, or 99 wt. % (e.g., with the balance being minor impurities such as water). In embodiments where the first reactant stream and the second reactant stream are the same physical feed to the reaction vessel (e.g., co-fed through a single inlet), the carboxylic acid concentration will be lower, generally corresponding to the desired carboxylic acid:hydroxy acid feed ratio along with any diluent (e.g, water) for the hydroxy acid.

In an embodiment, a molar excess of the carboxylic acid relative to the hydroxy acid is fed to the reaction vessel (e.g., across all feed stream(s) in the aggregate) to promote increased conversion of the hydroxy acid limiting reactant to the acyloxy carboxylic acid compound (e.g., based on thermodynamic equilibrium constraints for a particular carboxylic acid-hydroxy acid reaction system). The disclosed continuous reactive distillation process has an advantage that continuous product removal (e.g., acyloxy carboxylic acid compound product removal from the bottoms and water removal from the overhead) permits relatively higher levels of hydroxy acid conversion and acyloxy carboxylic acid compound yield at relatively lower levels of excess carboxylic acid. For example, suitable conversions and/or yields (described below) can be obtained when the ratio of the carboxylic acid to the hydroxy acid fed to the reaction vessel is at least 1:1, 1.5:1, 2:1, or 3:1 and/or up to 4:1, 5:1, 6:1, 8:1, or 10:1 (e.g., comparing the carboxylic acid content of the second reactant stream with the hydroxy acid content of the first reactant stream or the two components as fed to the reaction vessel in all stream(s)).

Some previous processes for forming acyloxy carboxylic acid compound have used non-acid carboxylate derivatives such as anhydrides or acyl halides of the carboxylic acid (e.g., acetic anhydride or acetyl chloride, respectively) as the process reactant for esterification of the hydroxy acid to avoid water formation as a condensation byproduct. Similar processes also have used entraining agents or water azeotrope-forming agents (e.g., benzene, hexane, chloroform, ligroin, petroleum ether, ethylene dichloride, and others that are non-reactive with reaction components) to provide a means for water byproduct removal. An advantage of the disclosed process is that the carboxylic acid can be used in its acid form (e.g., the system is free from non-acid carboxylate derivatives, which are generally more expensive than the acid) and need not use an entraining agent, in particular based on the continuous water removal of the disclosed reactive distillation process.

Products

The acyloxy carboxylic acid compound formed in the disclosed process is an ester reaction product between the acid functional group of the carboxylic acid reactant and the hydroxyl group of the hydroxy acid reactant. The carboxylic functional group of the hydroxy acid generally remains unchanged in the reaction (e.g., remaining in acid form or in a derivative form such as an ester, depending on the form in which it was fed to the reaction vessel). Thus, a hydroxy acid reactant in the form of an α-hydroxy carboxylic acid compound yields a corresponding 2-acyloxy carboxylic acid compound, and a hydroxy acid reactant in the form of an β-hydroxy carboxylic acid compound yields a corresponding 3-acyloxy carboxylic acid compound, where the acyloxy carboxylic acid compound can be in the acid or acid derivative form.

A representative structure of a 2-acyloxy carboxylic acid compound according to the disclosure is shown in Formula III.A below:

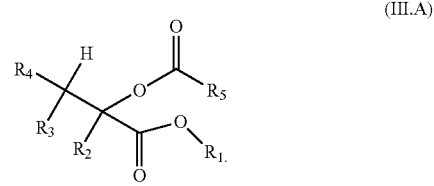

(III.A)

A representative structure of a 3-acyloxy carboxylic acid compound according to the disclosure is shown in Formula III.B below:

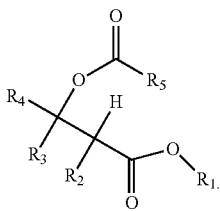
(III.B)

In Formulas III.A and III.B, $R_1$-$R_5$ can be independently selected from the various corresponding groups in Formulas I.A, I.B, and II above.

The first product stream (e.g., as withdrawn from the bottoms of the reactive distillation column) includes the acyloxy carboxylic acid compound product and can include additional components such as unreacted excess carboxylic acid, unreacted hydroxy acid (including monomeric and oligomeric forms thereof), and oligomeric forms of the acyloxy carboxylic acid compound (e.g., resulting from carboxylic acid esterification of the corresponding oligomeric hydroxy acid). The acyloxy carboxylic acid compound and the unreacted excess carboxylic acid are suitably the major components of the first product stream, for example where each can independently have a concentration of at least 10 wt. %, 20 wt. %, 30 wt. % or 40 wt. % and/or up to 50 wt. %, 60 wt. %, 70 wt. %, 80 wt. %, or 90 wt. %. In an embodiment, the acyloxy carboxylic acid compound is separated from the unreacted carboxylic acid in a downstream unit operation (e.g., distillation to provide a more concentrated acyloxy carboxylic acid compound product and a carboxylic acid reactant recycle) to provide a substantially pure acyloxy carboxylic acid compound (e.g., at least 95 wt. %, 98 wt. %, or 99 wt. % purity of desired monomeric product).

Continuous reactive distillation allows continuous removal of water from the reaction system, whether present as a feed component (e.g., feed diluent or impurity) or formed as a condensation byproduct. Water removal also provides a first product stream with a low water content, thus limiting or preventing acyloxy carboxylic acid compound product decomposition/hydrolysis (e.g., upon subsequent distillation separation from the unreacted carboxylic acid). Thus, product stream(s) including the acyloxy carboxylic acid compound are suitably substantially free from water. In an embodiment, the first product stream has a water concentration of 1 wt. %, 0.5 wt. %, 0.2 wt. %, 0.1 wt. %, 0.08 wt. %, 0.05 wt. %, or 0.03 wt. % or less (e.g., representing upper acceptable levels to limit undesirable hydrolysis of the product) and/or at least 0.0001 wt. %, 0.001 wt. %, or 0.01 wt. % (e.g., representing practical lower limits based on reaction vessel size). Such water levels are desirable from a cost-efficiency view; the water level can be further reduced as desired (e.g., using a larger reactive distillation column) in a given application. The water concentration can be relative to the first product stream as a whole or just the acyloxy carboxylic acid compound product. Desirably, the water level is low enough to achieve a product purity of 99% or higher.

Continuous reactive distillation also permits formation of advantageous water concentration gradients within the reaction vessel. In an embodiment, water is present in a local region of the reactive distillation column where substantial (unreacted) hydroxy acid is present; the presence of a sufficient amount of water can reduce undesired in situ oligomerization of the hydroxy acid in the reaction vessel (i.e., which would contribute additional oligomer to that fed to the reaction vessel). For example, in regions of the reaction vessel where the hydroxy acid has a substantial local concentration (e.g., at least 1%, 2%, 5%, or 10% on a weight or molar basis), the presence of local water can reduce or prevent further oligomerization. This reflects similar concentration gradients of the hydroxy acid and water in the reaction vessel: both concentrations are lower near the bottom of the column and both concentrations are higher near the top of the column (i.e., based on continuous hydroxy acid consumption and water removal, respectively).

In an embodiment, the first product stream has a low oligomer content with respect to oligomers of the acyloxy carboxylic acid compound (i.e., which may be formed during reaction between oligomers of the hydroxy acid feed and the carboxylic acid feed). The first product stream (or more generally any/all product streams exiting the reaction vessel) suitably has an acyloxy carboxylic acid compound oligomer content of 10%, 5%, 2%, or 1% or less and/or at least 0.1%, 0.2%, 0.5%, or 1% (e.g., generally representing the corresponding hydroxy acid oligomers fed to the reaction vessel as well as oligomeric species formed in situ during reaction). The acyloxy carboxylic acid compound oligomer content can be expressed on a weight basis or a molar basis, either relative to just the monomer content of the product stream(s) or all combined monomeric and oligomeric forms in the product stream(s).

The disclosed processes also provide reaction systems characterized by high reactant conversions and product yields. The conversion of the hydroxy acid is suitably at least 95%, 96%, 97%, 98%, 99%, 99.5%, or essentially 100%, which can be expressed on a mol. % or wt. % basis relative to the total amount of hydroxy acid reactant fed to the reaction vessel. Alternatively, 5%, 4%, 3%, 2%, 1%, or 0.5% or less of the hydroxy acid fed to the reaction vessel exits the reaction vessel via any product stream. The conversion can be based on a comparison of the monomeric form of the hydroxy acid entering and exiting the reaction vessel, or it can be based on all monomeric and oligomeric forms of the hydroxy acid. The yield of the acyloxy carboxylic acid compound is suitably at least 80%, 85%, 90%, 95%, 96%, 97%, 98%, or 99%, expressed on a mol. % or wt. % basis relative to the total amount of hydroxy acid fed to or reacted in the reaction vessel (e.g., assuming complete conversion of the hydroxy acid to the desired acyloxy carboxylic acid compound as a reference). The yield is generally based on the amount of monomeric acyloxy carboxylic acid compound product recovered in the first product stream (e.g., in a form corresponding to that of the hydroxy acid feed without additional (trans)esterification or other derivitization), and it can be relative to the monomeric form of the hydroxy acid entering the reaction vessel, or it can be relative to all monomeric and oligomeric forms of the hydroxy acid.

The second product stream (e.g., as withdrawn from the overhead of the reactive distillation column) generally includes unreacted carboxylic acid and water (e.g., fed to or formed in the reaction vessel) and can include additional components such as minor amounts of unreacted hydroxy acid and the acyloxy carboxylic acid compound product. The water and the unreacted excess carboxylic acid are suitably the major components of the first product stream, for example where each can independently have a concentration of at least 1 wt. %, 5 wt. %, 10 wt. %, 20 wt. %, 30 wt. % or 40 wt. % and/or up to 50 wt. %, 60 wt. %, 70 wt. %, 80 wt. %, 90 wt. %, 95 wt. %, or 99 wt. %. In an embodiment, the carboxylic acid content is relatively low, for example 1 wt. %, 5 wt. %, 10 wt. %, or 15 wt. % or less (e.g., with water being at least 85 wt. %, 90 wt. %, 95 wt. %, or 99 wt. %). In another embodiment, the water is separated from the unreacted carboxylic acid in a downstream unit operation (e.g., distillation to provide a carboxylic acid reactant recycle).

EXAMPLES

The following examples illustrate the disclosed processes and compositions, but are not intended to limit the scope of any claims thereto.

Examples 1-23

Formation of 2-Acetoxy Propanoic Acid

Examples 1-23 illustrate the production of 2-acetoxy-propionic acid (APA) using reactive distillation. The desired reaction involves acetylation of the 2-hydroxyl group on lactic acid with acetic acid to produce APA. The APA formed can be selectively decomposed to form acrylic acid (via a subsequent pyrolysis step), a commodity monomer with wide use in industrial and consumer applications, and to liberate the acetic acid which can be reused. See Lilga et al. U.S. Pat. No. 6,992,209, Smith (1942), Fisher (1944), and Ratchford (1945) related to the formation of acrylic acid or methyl acrylate. The examples illustrate a process that facilitates the efficient production of higher yields of a desired acyloxy carboxylic acid product from a hydroxy acid and carboxylic acid feed with less waste and potentially lower cost.

Overview: Examples 1-23 illustrate the use of relatively low acetic acid to lactic acid molar ratios (e.g., generally ranging from about 1.5:1 to 8:1), thus minimizing waste and/or recycling requirements of acetic acid. Reactive distillation allows removal of reaction products (water and APA) as they are formed, thus driving the reaction to completion without the use of a large excess of acetic acid. A glass reactive distillation column with a solid ion exchange resin catalyst (AMBERLYST 15) was used in the examples to convert lactic acid and produce good yields of monomer APA, thus demonstrating that ion exchange resins are effective catalysts for acyloxy carboxylic acid formation from hydroxy acids and carboxylic acids.

Further, producing APA in batch or continuous (i.e., non-reactive distillation) reactors requires subsequent separation of the APA product from water and excess reactants. With this downstream separation, partial hydrolysis of APA due to reaction with water can occur, and thus only relatively low yields of APA would be achieved as a result of subsequent product degradation. Such hydrolysis of APA with water is uncatalyzed (i.e., taking place without a catalyst such as sulfuric acid or an AMBERLYST resin present), so it is difficult to avoid in the purification of APA via conventional means. In the illustrated reactive distillation process, in contrast, it is possible to obtain product APA in a mixture containing primarily acetic acid, with negligible quantities of water, such that hydrolysis is avoided in a subsequent purification of APA (e.g., APA/acetic acid separation) and a high yield of pure APA can be obtained. In situ hydrolysis reactions within the reactive distillation column can be avoided via short reaction times and removal of water, thus permitting a reaction temperature at the bubble point of the liquid in the column (e.g., around 120° C.), thus giving significantly higher reaction rates than at the temperatures used in previous methods (e.g., 80° to 100° C.).

The examples further illustrate an unexpected aspect of the reactive distillation process for forming APA in the ability to achieve nearly quantitative APA yields (e.g., at least 96% of theoretical) using a dilute lactic acid feed (e.g., about 20% by weight in water). Because lactic acid is formed in fermentation at maximum concentrations of around 10-12 wt. % in solution, this result means that substantially less effort must be spent on concentrating a stock solution of lactic acid prior to conversion to APA than what would have been thought. The high lactic acid conversions achieved (nearly 100% in every experiment) were unexpected, and the ability to achieve high (>96%) APA yields from dilute feeds, essentially by avoiding uncatalyzed hydrolysis reactions in the reactive distillation column, was thought not to be possible, in particular given the potential APA hydrolysis and decomposition based on the presence of a substantial amount of water fed to the reaction system (i.e., as a lactic acid diluent).

Reactive Distillation: use of reactive distillation for APA formation employed a reactive distillation (RD) column 100 (FIG. 1) containing an AMBERLYST ion exchange resin as an acid catalyst. The catalyst was placed in the middle sections 130 of the column 110 such that there were uncatalyzed sections 140, 150 for separation both above and below the catalyst. Lactic acid 110 was fed to the RD column at the top of the catalyzed section, and acetic acid 120 was fed to the column at the bottom of the RD section. The goal of operation of the RD column is to drive water to the top 210 of the column, away from the APA product which goes to the bottom 310 of the column as it is formed. Such operation provides synergistic benefits, including a low local water concentration in the vicinity of higher APA product concentrations (i.e., which limits product decomposition) and a higher local water concentration in the vicinity of higher lactic acid concentration (i.e., which limits reactant oligomerization), notwithstanding the addition of water as a feed diluent to the reaction vessel.

The results of using reactive distillation to form APA, including feed rates, column configuration, product yields, temperatures, feed compositions, product compositions, internal column compositions, etc. are summarized in Tables 1-5 below. Tables 1-5 below give the conditions, results, and yields of APA achieved in the 23 reactive distillation experiments conducted. In these tables, it is seen that in most cases nearly 100% conversion of lactic acid is achieved, and APA yields as high as 96% are obtained. These results show that the use of reactive distillation for APA formation is effective.

TABLE 1

Examples 1-23: Inlet Component Distributions

| Run | LA Feed Conc | AA:LA Ratio | LA soln Feed Rate (g/min) | LA Feed Components (wt %) | | | | | | AA soln Feed Rate (g/min) | AA Feed Components (wt %) | | | | | |
|---|---|---|---|---|---|---|---|---|---|---|---|---|---|---|---|---|
| | | | | L1 | L2 | L3 | L4 | AA | W | | L1 | L2 | L3 | L4 | AA | W |
| 1 | 50 | 4.3 | 10.8 | 48.1 | 2.8 | 0 | 0 | 0 | 49.0 | 15.8 | 0 | 0 | 0 | 0 | 99.8 | 0.2 |
| 2 | 50 | 5.2 | 9.4 | 48.1 | 2.8 | 0 | 0 | 0 | 49.0 | 16.6 | 0 | 0 | 0 | 0 | 99.8 | 0.2 |

TABLE 1-continued

Examples 1-23: Inlet Component Distributions

| Run | LA Feed Conc | AA:LA Ratio | LA soln Feed Rate (g/min) | LA Feed Components (wt %) | | | | | | AA soln Feed Rate (g/min) | AA Feed Components (wt %) | | | | | |
|---|---|---|---|---|---|---|---|---|---|---|---|---|---|---|---|---|
| | | | | L1 | L2 | L3 | L4 | AA | W | | L1 | L2 | L3 | L4 | AA | W |
| 3 | 50 | 4.3 | 9.2 | 48.1 | 2.8 | 0 | 0 | 0 | 49.0 | 13.6 | 0 | 0 | 0 | 0 | 99.8 | 0.2 |
| 4 | 85 | 4.6 | 8.8 | 60.3 | 17.9 | 4.0 | 0.7 | 0 | 17.1 | 23.1 | 0 | 0 | 0 | 0 | 99.8 | 0.2 |
| 5 | 85 | 7.4 | 8.4 | 60.3 | 17.9 | 4.0 | 0.7 | 0 | 17.1 | 35.3 | 0 | 0 | 0 | 0 | 99.8 | 0.2 |
| 6 | 85 | 2.0 | 10.1 | 60.3 | 17.9 | 4.0 | 0.7 | 0 | 17.1 | 11.2 | 0 | 0 | 0 | 0 | 99.8 | 0.2 |
| 7 | 50 | 2.8 | 9.4 | 48.1 | 2.8 | 0 | 0 | 0 | 49.0 | 9.0 | 0 | 0 | 0 | 0 | 99.8 | 0.2 |
| 8 | 85 | 1.2 | 25.0 | 60.3 | 17.9 | 4.0 | 0.7 | 0 | 17.1 | 17.5 | 0 | 0 | 0 | 0 | 99.8 | 0.2 |
| 9 | 20 | 9.3 | 10.6 | 19.1 | 0.22 | 0 | 0 | 0 | 80.7 | 12.7 | 0 | 0 | 0 | 0 | 99.8 | 0.2 |
| 10 | 50 | 3.6 | 11.0 | 46.3 | 1.11 | 0 | 0 | 0 | 52.6 | 12.5 | 0 | 0 | 0 | 0 | 99.8 | 0.2 |
| 11 | 50 | 2.9 | 9.5 | 46.3 | 1.11 | 0 | 0 | 0 | 52.6 | 8.7 | 0 | 0 | 0 | 0 | 99.8 | 0.2 |
| 12 | 20 | 5.0 | 15.6 | 19.1 | 0.22 | 0 | 0 | 0 | 80.7 | 10.2 | 0 | 0 | 0 | 0 | 99.8 | 0.2 |
| 13 | 20 | 5.4 | 15.0 | 19.1 | 0.22 | 0 | 0 | 0 | 80.7 | 10.5 | 0 | 0 | 0 | 0 | 99.8 | 0.2 |
| 14 | 20 | 6.7 | 10.6 | 20.7 | 0.23 | 0 | 0 | 0 | 79.0 | 10.0 | 0 | 0 | 0 | 0 | 99.8 | 0.2 |
| 15 | 80 | 1.4 | 22.9 | 61.8 | 15.6 | 3.0 | 0.4 | 0 | 19.1 | 17.7 | 0 | 0 | 0 | 0 | 99.8 | 0.2 |
| 16 | 80 | 1.7 | 22.8 | 61.8 | 15.6 | 3.0 | 0.4 | 0 | 19.1 | 21.6 | 0 | 0 | 0 | 0 | 99.8 | 0.2 |
| 17 | — | 1.4 | — | — | — | — | — | — | — | 22.94* | 4.88 | 2.92 | 0.69 | 0.31 | 42.8 | 0.3 |
| 18 | 80 | 5.0 | 9.3 | 74.2 | 6.49 | 0.3 | 0 | 0 | 19.0 | 25.7 | 0 | 0 | 0 | 0 | 99.8 | 0.2 |
| 19 | 80 | 3.2 | 9.2 | 74.7 | 6.80 | 0.4 | 0 | 0 | 18.1 | 16.4 | 0 | 0 | 0 | 0 | 99.8 | 0.2 |
| 20 | 80* | 4.3 | 20.33* | 22.4 | 1.96 | 0.1 | 0 | 70.4 | 5.2 | — | — | — | — | — | — | — |
| 21 | 20 | 7.1 | 10.9 | 21.1 | 0.24 | 0 | 0 | 0 | 78.7 | 11.0 | 0 | 0 | 0 | 0 | 99.8 | 0.2 |
| 22 | 50 | 6.7 | 10.6 | 49.5 | 2.63 | 0 | 0 | 0 | 47.8 | 24.8 | 0 | 0 | 0 | 0 | 99.8 | 0.2 |
| 23 | 50* | 3.1 | 25.39* | 23.3 | 1.33 | 0.1 | 0 | 50.9 | 24.4 | — | — | — | — | — | — | — |

Note:
"LA Feed Conc." Reflects the nominal total lactic acid feed (i.e, including lactic acid monomer and oligomer(s) combined, relative to the amount of water fed). The "*" denotes a co-feed of LA and AA in a single stream. Asterisked LA feed concentrations are prior to premixing. Asterisked feed rates denote the total feed rate of the single feed. "AA soln feed rate" denotes a co-feed at the bottom feed port.
"LA soln feed rate" denotes a co-feed at the top feed port. Run 17 includes a single feed stream at the lower column portion generally corresponding to the AA feed position, and the feed corresponds to the reboiler composition of Run 16, further including APA (30.5%), L2APA (12.2%), L3APA (4.2%), and L4APA (1.3%).

TABLE 2

Examples 1-23: Reaction Conditions, Yields, and Material Balance Closure

| Run | Temperature (° C.) | | | | | LA Conv. (%) | L1APA Yield | Lactate balance closure | Acetate balance closure | Water balance closure |
|---|---|---|---|---|---|---|---|---|---|---|
| | LA Feed | AA Feed | Dist. | Column | Reboiler | | | | | |
| 1 | 105 | 100 | 100 | 101-119 | 127 | 54.2 | 31.6 | 85.1 | 80.0 | 117.9 |
| 2 | 105 | 100 | 100 | 101-119 | 127 | 100 | 74.5 | 84.2 | 106.8 | 69.4 |
| 3 | 105 | 100 | 100 | 101-121 | 135 | 97.5 | 80.0 | 96.2 | 92.9 | 106.4 |
| 4 | 105 | 100 | 105 | 105-121 | 137 | 96.4 | 68.9 | 107.3 | 95.2 | 179.2 |
| 5 | 105 | 100 | 107 | 107-120 | 130 | 100 | 54.4 | 94.6 | 89.7 | 114.2 |
| 6 | 105 | 100 | 101 | 101-125 | 175 | 97.8 | 53.8 | 98.0 | 100.1 | 107.6 |
| 7 | 105 | 100 | 100 | 100-122 | 167 | 96.0 | 80.8 | 107.1 | 102.5 | 95.9 |
| 8 | 105 | 100 | 100 | 100-129 | 170 | 74.5 | 43.3 | 105.5 | 98.7 | 89.4 |
| 9 | 100 | 105 | 102 | 102-121 | 165 | 100 | 85.9 | 114.4 | 93.5 | 104.5 |
| 10 | 100 | 105 | 82 | 101-122 | 147 | 99.8 | 82.8 | 101.4 | 97.1 | 101.7 |
| 11 | 100 | 105 | 102 | 102-123 | 162 | 98.8 | 78.5 | 103.3 | 100.5 | 98.5 |
| 12 | 25 | 105 | 100 | 102-119 | 134 | 86.5 | 92.8 | 112.8 | 99.3 | 91.0 |
| 13 | 100 | 105 | 98 | 99-119 | 132 | 88.7 | 88.8 | 105.3 | 94.3 | 92.6 |
| 14 | 100 | 105 | 100 | 100-119 | 136 | 97.2 | 96.4 | 105.8 | 104.4 | 96.2 |
| 15 | 109 | 107 | 101 | 101-131 | 181 | 86.0 | 47.0 | 100.3 | 101.1 | 96.9 |
| 16 | 107 | 102 | 107 | 116-130 | 183 | 90 | 47.5 | 99.1 | 97.2 | 100.2 |
| 17 | — | 105 | 114 | 115-134 | 184 | 53.6 | — | 103.2 | 100.3 | 93.0 |
| 18 | 100 | 105 | 110 | 119-126 | 138 | 97.3 | 65.0 | 100.2 | 97.1 | 109.0 |
| 19 | 100 | 105 | 109 | 119-125 | 142 | 91.3 | 56.8 | 97.9 | 98.1 | 100.9 |
| 20 | 100 | — | 106 | 106-121 | 139 | 58.1 | 52.8 | 113.2 | 93.5 | 86.4 |
| 21 | 100 | 105 | 99 | 99-119 | 131 | 98.0 | 93.4 | 99.9 | 97.5 | 97.5 |
| 22 | 105 | 102 | 101 | 103-119 | 129 | 97.3 | 84.4 | 98.7 | 97.8 | 106.3 |
| 23 | 100 | — | 101 | 101-110 | 128 | 24.8 | 20.7 | 100.8 | 98.5 | 93.3 |

TABLE 3

Examples 1-23: Distillate Product Distributions

| Run | Distillate Rate (g/min) | Distillate Products (wt %) | | | |
|---|---|---|---|---|---|
| | | Water | Acetic | L1 | APA |
| 1 | 6.76 | 99.98 | 0 | 0 | 0 |
| 2 | 6.76 | 58.00 | 42.00 | 0 | 0 |
| 3 | 8.60 | 72.00 | 28.00 | 0 | 0 |
| 4 | 13.35 | 37.30 | 61.60 | 0 | 1.01 |
| 5 | 18.68 | 18.40 | 80.00 | 0 | 1.60 |
| 6 | 9.15 | 38.50 | 59.20 | 0 | 2.30 |
| 7 | 9.59 | 58.80 | 41.00 | 0.03 | 0.02 |
| 8 | 10.40 | 72.40 | 27.50 | 0 | 0.11 |
| 9 | 19.03 | 49.17 | 50.83 | 0 | 0 |
| 10 | 11.84 | 58.82 | 40.91 | 0 | 0.23 |
| 11 | 9.86 | 59.16 | 40.71 | 0 | 0.14 |
| 12 | 14.38 | 83.27 | 16.58 | 0 | 0 |
| 13 | 13.10 | 89.83 | 10.17 | 0 | 0 |
| 14 | 13.06 | 65.11 | 34.89 | 0 | 0 |
| 15 | 13.05 | 56.80 | 43.00 | 0 | 0.18 |
| 16 | 16.92 | 45.30 | 53.73 | 0.45 | 0.52 |
| 17 | 7.98 | 4.16 | 92.84 | 0 | 2.87 |
| 18 | 15.74 | 22.53 | 76.64 | 0 | 0.81 |
| 19 | 8.80 | 36.07 | 61.58 | 1.20 | 1.11 |
| 20 | 7.34 | 22.71 | 77.22 | 0 | 0.05 |
| 21 | 12.46 | 70.66 | 29.25 | 0 | 0 |
| 22 | 12.18 | 54.03 | 45.97 | 0 | 0 |
| 23 | 13.07 | 48.93 | 51.06 | 0 | 0 |

TABLE 4

Examples 1-23: Bottoms Product Distributions

| Run | Bottoms Rate (g/min) | Bottoms Products (Wt %) | | | | | | | | | |
|---|---|---|---|---|---|---|---|---|---|---|---|
| | | Acetic | L1 | L2 | L3 | L4 | APA | L2APA | L3APA | L4APA | Water |
| 1 | 17.7 | 63.89 | 10.86 | 2.61 | 0.40 | 0.06 | 14.46 | 2.33 | 0.30 | 0.03 | 4.33 |
| 2 | 17.7 | 70.00 | 0 | 0 | 0 | 0 | 29.9 | 3.00 | 0 | 0 | 0 |
| 3 | 14.01 | 53.40 | 0.53 | 0.20 | 0.03 | 0.04 | 40.30 | 4.90 | 0.40 | 0 | 0 |
| 4 | 19.94 | 47.50 | 0.87 | 0.43 | 0 | 0 | 38.30 | 10.80 | 0.55 | 0.43 | 0 |
| 5 | 22.67 | 59.70 | 0 | 0 | 0 | 0 | 26.20 | 10.10 | 3.00 | 0.40 | 0 |
| 6 | 12.21 | 14.10 | 0.50 | 1.10 | 0 | 0 | 58.50 | 5.60 | 1.70 | 0 | 0 |
| 7 | 8.79 | 23.20 | 1.30 | 0.60 | 0.10 | 0.06 | 65.30 | 12.10 | 1.34 | 0.14 | 0 |
| 8 | 31.26 | 19.20 | 8.30 | 5.60 | 1.80 | 0.65 | 43.70 | 18.10 | 6.90 | 2.40 | 0 |
| 9 | 4.02 | 20.30 | 0 | 0 | 0 | 0 | 63.70 | 12.90 | 2.90 | 0.20 | 0 |
| 10 | 11.53 | 35.50 | 0 | 0.10 | 0 | 0 | 54.80 | 8.30 | 1.00 | 0 | 0 |
| 11 | 8.42 | 23.50 | 0.30 | 0.20 | 0 | 0.10 | 61.70 | 12.50 | 1.60 | 0.10 | 0.02 |
| 12 | 10.5 | 54.92 | 3.28 | 0.4 | 0 | 0 | 39.08 | 2.02 | 0.09 | 0 | 0.2 |
| 13 | 11.24 | 60.30 | 2.70 | 0.20 | 0 | 0 | 33.70 | 1.50 | 0 | 0 | 0.09 |
| 14 | 7.76 | 56.51 | 0.55 | 0.16 | 0.07 | 0 | 40.54 | 1.94 | 0.09 | 0.09 | 0.04 |
| 15 | 27.86 | 14.68 | 3.84 | 3.69 | 0.99 | 0.41 | 47.00 | 19.98 | 7.71 | 1.54 | 0.16 |
| 16 | 27.05 | 13.27 | 2.40 | 2.98 | 0.57 | 0.30 | 48.50 | 22.13 | 8.45 | 1.30 | 0.11 |
| 17 | 15.38 | 13.26 | 1.83 | 3.41 | 0.50 | 0.20 | 43.78 | 24.08 | 10.48 | 2.38 | 0.09 |
| 18 | 19.1 | 46.03 | 0.49 | 0.37 | 0.11 | 0.03 | 37.40 | 11.60 | 2.73 | 0.09 | 0.15 |
| 19 | 16.57 | 42.42 | 1.93 | 0.96 | 0.26 | 0.05 | 37.80 | 12.83 | 3.55 | 0.15 | 0.04 |
| 20 | 12.68 | 44.61 | 11.82 | 3.42 | 0.71 | 0.13 | 30.62 | 6.55 | 1.50 | 0.09 | 0.54 |
| 21 | 8.94 | 62.58 | 0.33 | 0.07 | 0.06 | 0.04 | 35.59 | 1.27 | 0.02 | 0.01 | 0.03 |
| 22 | 22.99 | 66.29 | 0.38 | 0.17 | 0 | 0.08 | 29.90 | 2.90 | 0.23 | 0.02 | 0.03 |
| 23 | 12.50 | 40.77 | 28.82 | 6.79 | 1.20 | 0.19 | 15.32 | 2.42 | 0.35 | 0.01 | 4.13 |

TABLE 5

Examples 9-23: Internal Column Component Concentrations

| Run | Component | Internal Column Position (FIG. 2) | | | |
|---|---|---|---|---|---|
| | | I1 | I2 | I3 | I4 |
| 9 | LA | 6.11 | 0 | 0 | 0.94 |
| | APA | 1.99 | 7.77 | 9.27 | 17.13 |
| | Water | 6.91 | 0.33 | 0.23 | 0.26 |
| 10 | LA | 18.16 | 1.33 | 0.34 | 0.71 |
| | APA | 3.51 | 11.0 | 8.70 | 14.64 |
| | Water | 11.37 | 0.53 | 0.20 | 0.09 |
| 11 | LA | 21.0 | 1.09 | 0.37 | 0.67 |
| | APA | 3.58 | 12.3 | 12.6 | 18.5 |
| | Water | 12.2 | 0.82 | 0.36 | 0.53 |
| 12 | LA | 13.6 | 2.78 | 0.62 | 0.88 |
| | APA | 0.30 | 3.72 | 5.70 | 6.89 |
| | Water | 50.1 | 2.15 | 0.38 | 0.43 |
| 13 | LA | 16.3 | 2.48 | 0.72 | 0.73 |
| | APA | 0.23 | 2.74 | 5.55 | 5.87 |
| | Water | 55.8 | 2.29 | 0.35 | 0.17 |
| 14 | LA | 8.58 | 0.49 | 0 | 0 |
| | APA | 0.51 | 4.03 | 4.96 | 6.17 |
| | Water | 22.2 | 0.47 | 0.54 | 0.41 |
| 15 | LA | 39.5 | 8.35 | 4.08 | 6.28 |
| | APA | 4.05 | 17.1 | 19.0 | 29.0 |
| | Water | 8.62 | 2.19 | 0.99 | 0.58 |
| 16 | LA | 33.1 | 5.15 | 2.44 | 3.48 |
| | APA | 5.89 | 25.1 | 21.6 | 30.4 |
| | Water | 7.05 | 1.59 | 0.52 | 0.67 |
| 17 | LA | 0.73 | 0.52 | 0 | 3.18 |
| | APA | 6.32 | 3.18 | 1.48 | 32.4 |
| | Water | 1.68 | 1.54 | 1.57 | 0.34 |

TABLE 5-continued

Examples 9-23: Internal Column Component Concentrations

| Run | Component | Internal Column Position (FIG. 2) | | | |
|---|---|---|---|---|---|
| | | I1 | I2 | I3 | I4 |
| 18 | LA | 24.3 | 0.90 | 0.38 | 0.51 |
| | APA | 8.63 | 13.6 | 11.8 | 13.0 |
| | Water | 3.19 | 0.55 | 0.22 | 0.88 |
| 19 | LA | 29.0 | 1.24 | 0.52 | 0.71 |
| | APA | 8.71 | 11.4 | 11.9 | 15.0 |
| | Water | 5.09 | 0.93 | 0.36 | 0.22 |
| 20 | LA | 13.9 | 6.93 | 3.54 | 7.10 |
| | APA | 2.54 | 7.10 | 4.44 | 10.4 |
| | Water | 8.65 | 10.4 | 8.03 | 1.09 |
| 21 | LA | 10.5 | 0.72 | 0 | 0 |
| | APA | 0.39 | 3.72 | 4.89 | 5.30 |
| | Water | 27.6 | 0.60 | 0.12 | 0.04 |
| 22 | LA | 16.0 | 1.03 | 0 | 0 |
| | APA | 1.91 | 8.54 | 10.2 | 8.14 |
| | Water | 9.76 | 0.45 | 0.17 | 0.21 |
| 23 | LA | 22.4 | — | 18.3 | 17.0 |
| | APA | 1.58 | — | 4.69 | 4.65 |
| | Water | 23.6 | — | 21.7 | 9.48 |

Figure 2:
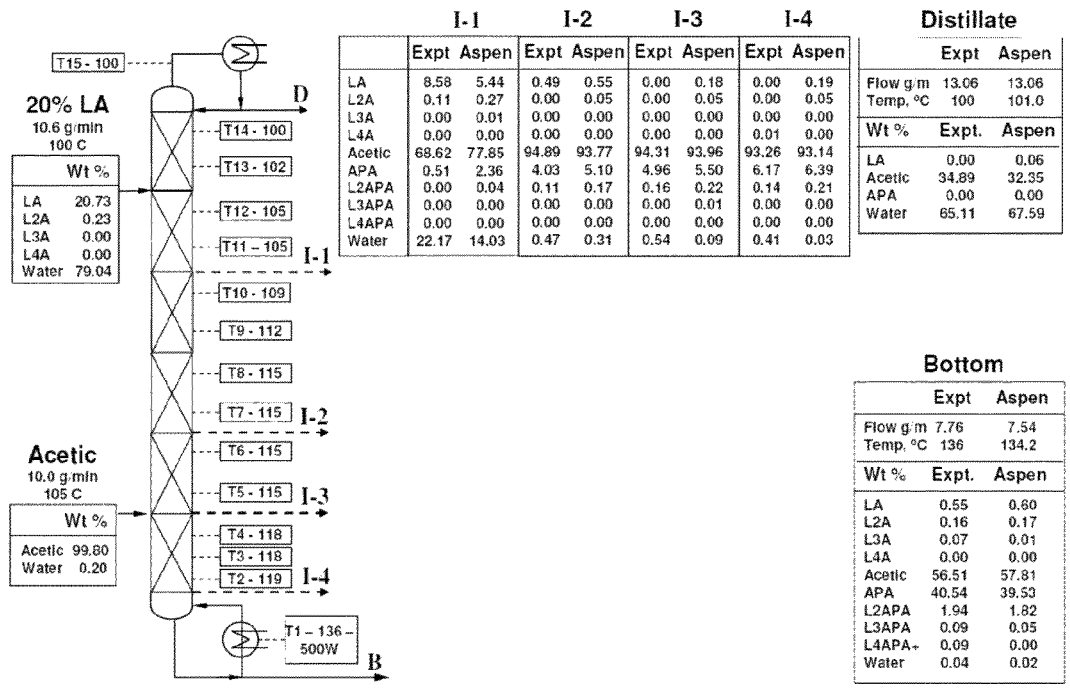
FIG. 2 illustrates detailed stream composition and temperature data for an example reactive distillation process according to the disclosure.

Abbreviations for Tables 1-5:
AA: acetic acid
LA: lactic acid (all monomeric and oligomeric forms combined)
L1: lactic acid in monomeric form
L1APA or APA: 2-acetoxy propanoic acid (i.e., acetoxy reaction product of monomeric lactic acid)
L2-L4: 2-, 3-, and 4-mer lactic acid oligomers, respectively
L2APA-L4APA: acetoxy reaction product of 2-, 3-, and 4-mer lactic acid oligomers, respectively
W: water A simplified presentation of results for Example 14 is given as FIG. 2. It shows the reactive distillation column on the left side. Each box in the column represents a one-meter section of column. The catalytic portion of the column, between the two feeds, is thus four meters in height, with a one-meter rectifying section above and a one meter stripping section below the catalyst section. Component concentrations for reactants and products both exiting the column (D, B) and at intermediate locations (I1, I2, I3, I4) within the column are given in the boxes to the right of the column. FIG. 2 further includes a comparison of measured and predicted (using ASPEN process simulation; available from Aspen Technology, Burlington, Mass.) stream concentrations (wt. %), concentration distributions within the reactive distillation column (wt. %), and temperature distributions (° C.) for the reactive distillation column.

Reboiler Temperature: The reboiler temperature was controlled by the power added to the reboiler of the column for a given feed scenario, and it determined the composition of the bottoms product. The bottoms product desirably contains negligible quantities of water and contained substantial quantities of acetic acid when the column is properly operated, the former in order to avoid hydrolysis reactions from water and the latter to avoid extremely high temperatures which result in product breakdown if acetic acid is not present in sufficient quantities.

A good comparison of similar experiments with different reboiler temperatures is illustrated in Examples 9 and 14. Both are run with 20 wt % lactic acid solutions at about 25 ml/min. In Example 9, a higher reboiler power was used and the reboiler temperature was 165° C., resulting in an APA yield of 86%. The bottoms product from this run contained 20 wt % acetic acid. In Example 14, a lower reboiler power and corresponding reboiler temperature of 136° C. allowed more acetic acid to remain in the reboiler (56% by weight), and thus APA yield increased to 96% because high temperatures and undesirable side reactions of APA were avoided. This shows the value of properly controlling reboiler temperature during reactive distillation: the increase in APA yield more than offsets the need to separate a larger amount of acetic acid from the APA product in a subsequent downstream separation process.

Lactic Acid Feed Concentration: The concentration of lactic acid fed to the column had an effect on APA formation, because more highly concentrated solutions of lactic acid contain substantial quantities of dimer and higher oligomers that convert to acetylated dimers (L2APA, etc.) in the RD column, thus reducing the yield of the desired product in monomeric form (i.e., APA). Examples 14 and 22, carried out at essentially the same reboiler temperature (about 130° C. to 135° C.) and acetic acid:lactic acid feed ratio (about 6.7), illustrate the effect of feed concentration: feeding 50 wt % lactic acid feed (Example 22) gave only 84% APA yield, while Example 14 with 20 wt % lactic acid feed gave a 96% APA yield. It is thus an advantageous and previously unconsidered approach to preferably feed dilute lactic acid to the reactive distillation column.

Examples 24-25

Preparation of Non-Equilibrium Lactic Acid

Examples 24-25 illustrate a method for producing a high monomer-content, concentrated lactic acid or other hydroxy acid (e.g., at least 50, 60 70, 80, or 90 wt. %) feed material for APA or acyloxy carboxylic acid formation via reactive distillation. This high monomer material is a metastable, non-equilibrium solution: if left alone, over time the lactic acid species will equilibrate by forming oligomers of different chain lengths and decreasing the amount of lactic acid in monomeric form. However, if the high monomer-content solution is used immediately or soon after preparation, the high monomer lactic acid could enhance APA monomer yield by providing a concentrated, low-oligomer source of lactic acid feed material.

Lactic acid (in addition to generalized hydroxy acids according to the disclosure) contains both a hydroxyl group and a carboxylic acid group, so it self-esterifies to form oligomers (dimers, trimers, etc.) in aqueous solution as water is progressively removed. This self-esterification reaction gives a well-defined equilibrium distribution of oligomers as a function of water content (Lira, 2007), where more concentrated solutions favor a higher fraction of oligomeric species and more dilute solutions favor a higher fraction of monomeric species.

In several reactive distillation experiments to form APA, the lactic acid fed had a low water content and thus contained a significant equilibrium concentration of lactic acid oligomers, which when exposed to acetic acid formed APA oligomers instead of the desired APA monomer. These APA oligomers are of uncertain value in terms of their ability to decompose into acrylic acid, and are thus undesirable products that potentially will result in loss of acrylate yield from the starting lactic acid.

To overcome this potential loss of yield, the disclosed process includes a method to reduce or eliminate the lactate oligomers in the feed solution to the reactive distillation column. This method is based on the fact that the rate of interconversion between oligomers, and thus the rate at which equilibration of oligomers takes place from an initial non-equilibrium distribution, is kinetically limited. For example, the equilibration of lactic acid may take several days at room temperature, but it takes only a few hours at 100° C.

The method utilizes the slower room-temperature (e.g., 20° C. to 25° C.) oligomerization kinetics to produce a non-equilibrated lactic acid solution containing a disproportionately large fraction of lactic acid monomer. This high monomer solution can be produced by diluting any lactic acid mixture to about 20 wt. % lactic acid/80 wt. % water, and then heating to rapidly equilibrate the lactic acid oligomers. At this low concentration of lactic acid, the equilibrium distribution of lactic acid oligomers greatly favors the monomer, such that only ~1% of lactic acid is present as dimer or trimer and the remaining ~99% of lactic acid is present as monomer. Once this diluted solution has been heated for several hours to facilitate equilibration, it can be cooled under vacuum to around 40° C. and it is possible, by removing nearly all water, to produce a highly concentrated solution (e.g., up to 95 wt. %) of lactic acid monomer with a low oligomer content.

Figure 3:
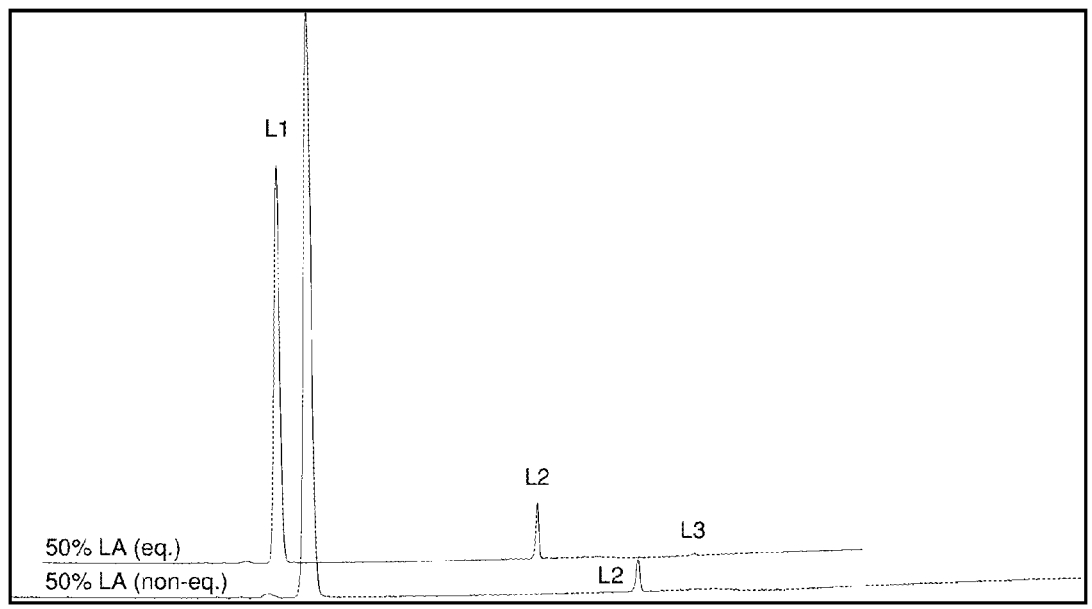
FIGS. 3 and 4 illustrate equilibrium and non-equilibrium lactic acid mixtures formed according to the disclosure (with "Ln" representing an n-mer lactic acid species).
Figure 4:
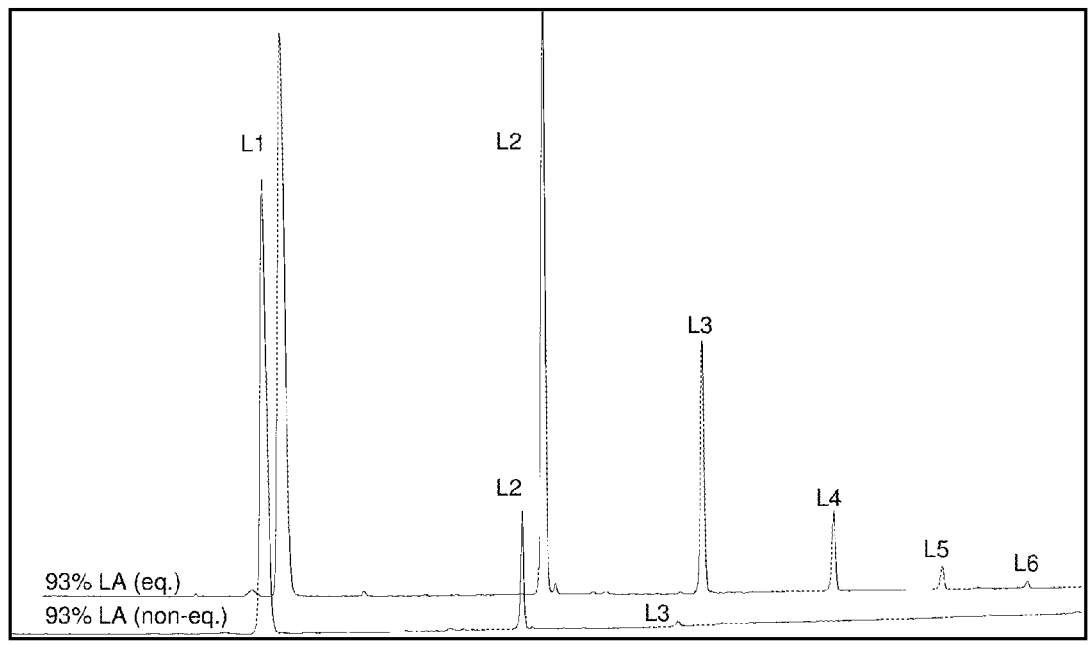

Commercial 50% lactic acid (20 L) was diluted to 20% with 30 L deionized water. Refluxing this 20% LA solution for 16 hours resulted in increasing the monomer fraction from 94.6% to 98.8%. Subsequent concentration to 50% in a 4" wiped film still at 25-40 Torr gave 98.5% monomer (Example 24). Further concentration to 93% gave 91.2% monomer compared to 59% equilibrium monomer fraction (Example 25). Table 6 below summarizes the results for Examples 24 and 25, and it illustrates that the reduced, non-equilibrium oligomer content of the obtained concentrated solutions is relatively small compared to the corresponding equilibrium oligomer content (i.e., "Fraction" entry in Table 6). FIG. 3 shows a chromatographic analysis of monomeric and oligomeric forms in a stock (equilibrated) 50% LA solution and a non-equilibrium 50% LA solution prepared by the method above. FIG. 4 compares the chromatogram of an equilibrium 93% LA solution and the solution prepared by the method above. Preferably, the concentrated, non-equilibrium lactic acid monomer solution is fed to the reactive distillation column within 24 hours (e.g., within 12, 6, 3, 2, or 1 hours) of its formation in order to ensure that substantial oligomerization does not occur. Alternatively or additionally, the non-equilibrium mixture can be stored under low-temperature conditions (e.g., at room temperature or lower, such as being chilled to point that preserves a liquid mixture) to limit the rate of equilibrium oligomerization if not used very soon after formation. If this is done, a very high yield of monomer APA can be achieved.

should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

REFERENCES

1. Filachione et al. U.S. Pat. No. 2,399,595
2. Miller et al. U.S. Pat. No. 6,713,640
3. Lilga et al. U.S. Pat. No. 6,992,209
4. Miller et al. U.S. Pat. No. 7,321,052
5. Smith et al., "Pyrolysis of Lactic Acid Derivatives," Industrial and Engineering Chemistry, vol. 34, no. 4, p. 473-479 (1942).
6. Fisher et al., "Methyl Acrylate Production by Pyrolysis of Methyl Acetoxypropionate," Industrial and Engineering Chemistry, vol. 36, no. 3, p. 229-234 (1944).
7. Ratchford et al., "Methyl Acrylate by Pyrolysis of Methyl Acetoxypropionate," Industrial and Engineering Chemistry, vol. 37, no. 4, p. 382-387 (1945).
8. Filachione et al., "Preparation of α-Carbalkoxyalkyl Methacrylates by Pyrolysis of the Corresponding α-Acetoxyisobutyrates," Industrial and Engineering Chemistry, vol. 70, p. 526-529 (1948).
9. Golomb et al., "The Acyl Derivatives and Lactides of Some α-Hydroxy-acids," Journal of the Chemical Society, p. 838-847 (1962).

TABLE 6

Examples 24-25: Equilibrium and Non-Equilibrium Monomer/Oligomer Content

| Example | LA Conc. | Equilibrium Content | | Non-Equilibrium Content | | Fraction |
| --- | --- | --- | --- | --- | --- | --- |
| | | Monomer | Oligomer | Monomer | Oligomer | |
| Reference | 20 wt. % | 98.8 wt. % | 1.2 wt. % | n/a | n/a | |
| 24 | 50 wt. % | 94.6 wt. % | 5.4 wt. % | 98.5 wt. % | 1.5 wt. % | 0.28 |
| 25 | 93 wt. % | 59 wt. % | 41 wt. % | 91.2 wt. % | 8.8 wt. % | 0.22 |

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations

What is claimed is:

1. A method for forming an acyloxy carboxylic acid or derivative thereof, the method comprising:
    (a) providing a first reactant stream comprising a hydroxy acid at a concentration ranging from 1 wt. % to 60 wt. %. the hydroxy acid being selected from the group consisting of an α-hydroxy carboxylic acid, a β-hydroxy carboxylic acid, an ester thereof, an amide thereof, and combinations thereof;
    (b) providing a second reactant stream comprising a carboxylic acid;

(c) feeding the first reactant stream and the second reactant stream to a reaction vessel comprising a continuous reactive distillation column and containing a catalyst comprising a solid acid catalyst;

(d) reacting the hydroxy acid and the carboxylic acid in the reaction vessel and in the presence of the catalyst to form a reaction product therebetween, the reaction product comprising an acyloxy carboxylic acid compound; and (e) removing a first product stream comprising the acyloxy carboxylic acid compound from the reaction vessel;

wherein a ratio of the carboxylic acid to the hydroxy acid fed to the reaction vessel ranges from 1:1 to 10:1; and the acyloxy carboxylic acid compound has a yield of at least 80%.

2. The method of claim 1, wherein the first product stream is substantially free from water.

3. The method of claim 1, wherein the reaction of the hydroxy acid and the carboxylic acid in the presence of the catalyst is performed substantially at or above the bubble point of a local mixture in the reaction vessel between the first reactant stream, the second reactant stream, and any reaction products therebetween.

4. The method of claim 1, wherein the hydroxy acid has a conversion of at least 95%.

5. The method of claim 1, wherein:
(i) the hydroxy acid comprises the α-hydroxy carboxylic acid compound; and
(ii) the reaction product comprises a 2-acyloxy carboxylic acid compound.

6. The method of claim 5, wherein:
(i) the α-hydroxy carboxylic acid compound comprises a first compound having the formula (I):

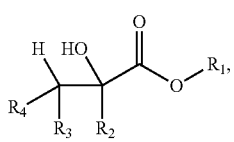

(I)

wherein:
(A) $R_1$ is selected from the group consisting of H, hydrocarbons containing from 1 to 20 carbon atoms, and heteroatom-substituted hydrocarbons containing from 1 to 20 carbon atoms, and
(B) each of $R_2$, $R_3$, and $R_4$ are independently selected from the group consisting of H, hydrocarbons containing from 1 to 20 carbon atoms, and heteroatom-substituted hydrocarbons containing from 1 to 20 carbon atoms;

(ii) the carboxylic acid comprises a second compound having the formula (II):

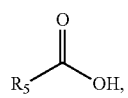

(II)

wherein $R_5$ is independently selected from the group consisting of H, hydrocarbons containing from 1 to 20 carbon atoms, and heteroatom-substituted hydrocarbons containing from 1 to 20 carbon atoms; and (iii) the 2-acyloxy carboxylic acid compound comprises a third compound having the formula (III):

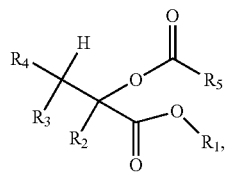

(III)

wherein $R_1$ to $R_5$ are as defined in formula (I) and formula (II).

7. The method of claim 5, wherein:
(i) the α-hydroxy carboxylic acid compound comprises lactic acid;
(ii) the carboxylic acid comprises acetic acid; and
(iii) the 2-acyloxy carboxylic acid compound comprises 2-acetoxy propanoic acid.

8. The method of claim 1, wherein:
(i) the hydroxy acid comprises the β-hydroxy carboxylic acid compound; and
(ii) the reaction product comprises a 3-acyloxy carboxylic acid compound.

9. The method of claim 8, wherein:
(i) the β-hydroxy carboxylic acid compound comprises 3-hydroxy propanoic acid;
(ii) the carboxylic acid comprises acetic acid; and
(iii) the 3-acyloxy carboxylic acid compound comprises 3-acetoxy propanoic acid.

10. The method of claim 1, wherein the catalyst comprises an acid catalyst.

11. The method of claim 1, wherein the catalyst comprises a solid acid catalyst.

12. The method of claim 1, wherein the first product stream has a water concentration of 0.1 wt. % or less.

13. The method of, claim 1, wherein water is present In a local region of the reactive distillation column where hydroxy acid is present, the water being present in an amount sufficient to reduce oligomerization of the hydroxy acid in the local region.

14. The method of, claim 1, wherein:
(i) the reaction vessel comprises (A) a first inlet positioned at a first elevation, (B) a second inlet positioned at a second elevation lower than the first elevation, (C) a first outlet positioned at a third elevation lower than the second elevation; and (D) optionally a second outlet position at a fourth elevation higher than the first elevation;
(ii) at least some of the solid acid catalyst is positioned in the reaction vessel between the first inlet and the second inlet;
(iii) the first reactant stream is fed to the reaction vessel through the first inlet;
(iv) the second reactant stream is fed to the reaction vessel through the second inlet;
(v) the first product stream is removed from the reaction vessel through the first outlet; and
(vi) the second product stream, when present, is removed from the reaction vessel through the second outlet.

15. The method of claim 1, wherein:
(i) the first product stream further comprises unreacted carboxylic acid; and
(ii) the method further comprises: (f) separating the acyloxy carboxylic acid compound from the unreacted carboxylic acid.

16. The method of claim 1, further comprising:
(f) removing a second product stream comprising unreacted carboxylic acid from the reaction vessel; and (g) recycling the second product stream to the reaction vessel to provide at least a portion of the carboxylic acid in the second reactant stream.

17. The method of claim 1, wherein the first reactant stream comprises a non-equilibrium mixture of the hydroxy acid and its associated oligomers.

18. The method of claim 17, wherein the oligomer content of the first reactant stream is 50% or less relative to the oligomer content of a corresponding equilibrium mixture of the hydroxy acid and its associated oligomers.

19. The method of claim 1, further comprising:
(f) removing a second product stream comprising unreacted carboxylic acid from the reaction vessel.

20. A method for forming an acyloxy carboxylic acid or derivative thereof, the method comprising:
(a) providing a first reactant stream comprising a hydroxy acid at a concentration ranging from 1 wt. % to 60 wt. %, the hydroxy acid being selected from the group consisting of an α-hydroxy carboxylic acid, a β-hydroxy carboxylic acid, an ester thereof, an amide thereof, and combinations thereof;
(b) providing a second reactant stream comprising a carboxylic acid;
(c) feeding the first reactant stream and the second reactant stream to a reaction vessel containing a catalyst;
(d) reacting the hydroxy acid and the carboxylic acid in the reaction vessel and in the presence of the catalyst to form a reaction product therebetween, the reaction product comprising an acyloxy carboxylic acid compound; and
(e) removing a first product stream comprising the acyloxy carboxylic acid compound from the reaction vessel;
wherein the first product stream is substantially free from water.

21. A method for forming an acyloxy carboxylic acid or derivative thereof, the method comprising:
(a) providing a first reactant stream comprising a hydroxy acid at a concentration ranging from 1 wt. % to 60 wt. %, the hydroxy acid being selected from the group consisting of an α-hydroxy carboxylic acid, a β-hydroxy carboxylic acid, an ester thereof, an amide thereof, and combinations thereof;
(b) providing a second reactant stream comprising a carboxylic acid;
(c) feeding the first reactant stream and the second reactant stream to a reaction vessel containing a catalyst;
(d) reacting the hydroxy acid and the carboxylic acid in the reaction vessel and in the presence of the catalyst to form a reaction product therebetween, the reaction product comprising an acyloxy carboxylic acid compound; and
(e) removing a first product stream comprising the acyloxy carboxylic acid compound from the reaction vessel;
wherein the reaction of the hydroxy acid and the carboxylic acid in the presence of the catalyst is performed substantially at or above the bubble point of a local mixture in the reaction vessel between the first reactant stream, the second reactant stream, and any reaction products therebetween.

22. A method for forming an acyloxy carboxylic acid or derivative thereof, the method comprising:
(a) providing a first reactant stream comprising a hydroxy acid at a concentration ranging from 1 wt. % to 60 wt. %, the hydroxy acid being selected from the group consisting of an α-hydroxy carboxylic acid, a β-hydroxy carboxylic acid, an ester thereof, an amide thereof, and combinations thereof;
(b) providing a second reactant stream comprising a carboxylic acid;
(c) feeding the first reactant stream and the second reactant stream to a reaction vessel containing a catalyst;
(d) reacting the hydroxy acid and the carboxylic acid in the reaction vessel and in the presence of the catalyst to form a reaction product therebetween, the reaction product comprising an acyloxy carboxylic acid compound; and
(e) removing a first product stream comprising the acyloxy carboxylic acid compound from the reaction vessel;
wherein the hydroxy acid has a conversion of at least 95%.

23. The method of, claim 1, wherein the hydroxy acid is selected from the group consisting of an α-hydroxy carboxylic acid, a β-hydroxy carboxylic acid, and combinations thereof.

24. The method of, claim 1, comprising reacting the hydroxy acid and the carboxylic acid in the reaction vessel in the absence of an entraining agent.

* * * * *